United States Patent [19]
Braun et al.

[11] Patent Number: 5,679,332
[45] Date of Patent: Oct. 21, 1997

[54] HAIR KERATIN-REDUCING CYSTEINE ESTERS AND COMPOSITIONS FOR PERMANENT SHAPING OF HAIR BASED ON SAME

[75] Inventors: Hans-Juergen Braun, Ueberstorf, Switzerland; Guenther Lang, Reinheim; Gerhard Maresch, Darmstadt, both of Germany

[73] Assignee: Wella Aktiengesellschaft, Darmstadt, Germany

[21] Appl. No.: 559,374

[22] Filed: Nov. 16, 1995

[30] Foreign Application Priority Data

Feb. 9, 1995 [DE] Germany .................. 195 04 215.8

[51] Int. Cl.[6] .................................................. A61K 7/09
[52] U.S. Cl. .................. 424/70.51; 514/550; 560/147
[58] Field of Search .................. 560/147; 514/550; 424/70.51

[56] References Cited

U.S. PATENT DOCUMENTS

| | | | |
|---|---|---|---|
| 4,153,681 | 5/1979 | Shiba | 424/70.51 |
| 4,218,435 | 8/1980 | Shiba | 424/70.51 |
| 4,992,267 | 2/1991 | DenBeste et al. | 424/70.51 |
| 5,500,210 | 3/1996 | Stomer et al. | 424/70.51 |
| 5,503,826 | 4/1996 | Lang et al. | 424/70.51 |
| 5,589,163 | 12/1996 | Neill et al. | 424/70.51 |

*Primary Examiner*—Amy Hulina
*Attorney, Agent, or Firm*—Micael J. Striker

[57] ABSTRACT

The hair shaping composition for permanent shaping of hair contains a cysteine ester of the formula (I):

$$HS-CH_2-CH(NH_2)-COO-CH_2-CH_2-R \quad (I)$$

as a keratin-reducing material, wherein R is a hydroxy group, alkoxy groups, a poly(alkoxy) group or a hydroxypoly(alkoxy) group, or one of its acid additional salts. Cysteine ester compounds and their methods of preparation are also described. Preferred embodiments of the hair shaping composition have a pH of from 4.5 to 9.0 and contain from 4 to 30% by weight of the cysteine ester or its acid addition salt and provide a safe and uniform shaping of hair without allergic or sensitizing reactions.

17 Claims, No Drawings

HAIR KERATIN-REDUCING CYSTEINE ESTERS AND COMPOSITIONS FOR PERMANENT SHAPING OF HAIR BASED ON SAME

Be it known that we, Hans-Jürgen Braun, Günther Lang and Gerhard Maresch, citizens of Germany, whose residences and post office addresses are, respectively, Kapellacker 10D, CH-3182 Ueberstorf, Switzerland; Auf der Roten Erde 10 B, D-64354 Reinhelm 5, Germany and Winkelschneise 6, D-64295 Darmstadt, Germany, have invented new and useful hair keratin-reducing cysteine esters and compositions for permanent shaping of hair based on same of which the following is a complete specification thereof:

BACKGROUND OF THE INVENTION

The present invention relates to new hair keratin-reducing cysteine esters and compositions for permanent shaping of hair containing hair keratin-reducing cysteine esters.

Weakly acidic to neutral permanent shaping compositions are used for a careful safe permanent shaping of damaged, particularly bleached or dyed hair. In the course of the last 30 years the thioglycolic acid esters have proven to be the best reducing agents for this application.

Hair shaping composition based on cysteine or cysteine ethyl ester and their salts can also be used for a permanent shaping of damaged hair. The pH of these compositions is in the mildly alkaline range of from about 7.1 to 9.

The safe permanent hair shaping treatment provided by weakly acidic to neutral shaping compositions however has a number of disadvantages. These compositions have a reduced effectiveness in comparison to mildly alkaline hair shaping compositions based on thioglycolate. For this reason it is necessary to supply heat, extend the composition acting time on the hair to from 20 to 60 minutes and to use comparatively thin curlers. Thus the use of these hair shaping agents for normal, undamaged natural hair does not seem to be reasonable because of the comparatively long required acting time with heating, so that the use of weakly acidic to neutral hair shaping compositions has up to now usually been limited to damaged, easily shaped hair.

The poor eye and skin compatibility and the sensitizing action of thioglycolic acid ester are additional considerable disadvantages for these acidic hair shaping compositions.

Inspite of the many attempts up to now the sensitizing action of acidic hair shaping compositions could not be significantly reduced. As an alternative thus mildly alkaline hair shaping compositions having a pH from 7.1 to 9 have been proposed which contain cysteine or its salts as the effective keratin-reducing agent.

These latter hair shaping compositions based on cysteine or its salts however similarly have a series of disadvantages. Thus cysteine has only a weak shaping effect and a reduced stability. If cysteine-containing shaping compositions are applied to hair, the cysteine is rapidly oxidized by the oxygen in the air to cystine which can only be dissolved in water with difficulty. The formation of cystine is troublesome because it forms a white coating on the hair which is difficult to remove.

The ease with which cysteine and/or its salts are oxidized makes its use in permanent shaping compositions almost impossible and currently can be improved, if at all, only by addition of suitable co-reducing agents.

SUMMARY OF THE INVENTION

It is an object of the present invention to provide a hair shaping composition for the permanent shaping of hair which allows a safe and uniform shaping in both the acid and the weakly alkaline pH range, i.e. a pH range of from 4.5 to 9.0, has no or only a reduced potential to cause allergies and does not form a troublesome deposit or coating on the hair.

It is another object of the invention to provide new cysteine esters useful in compositions for the permanent shaping of hair.

It has been found that unexpectedly a uniform shaping of both damaged and undamaged hair is possible using a hair shaping composition based on certain cysteine esters without causing the allergic skin reactions frequently observed with the currently known hair keratin-reducing ester compounds used in hair shaping compositions or the without producing the troublesome coating observed when cysteine-containing hair shaping compositions are used.

The subject matter of the present invention is thus a composition for the permanent shaping of hair based on a keratin-reducing material, which comprises at least one cysteine ester of the formula (I):

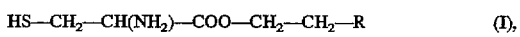

$$HS-CH_2-CH(NH_2)-COO-CH_2-CH_2-R \qquad (I),$$

wherein R=a hydroxy group, an alkoxy group, a poly (alkoxy) group or a hydroxypoly(alkoxy) group, or its acid additional salt.

In preferred embodiments of the invention the alkoxy group in the at least one cysteine ester has from 1 to 6 carbon atoms, the poly(alkoxy) group has the formula $\{O-(C_1-C_6\text{-alkyl})\}_nH$ in which the polymerization degree, n, is 2 to 20, especially from 2 to 10; or a hydroxypoly(alkoxy) group of the formula $\{O-(C_1-C_6\text{-alkyl})\}_mOH$ in which the polymerization degree, m, is from 1 to 20, particularly from 2 to 10. The expression $C_1-C_6$-alkyl designates an alkyl group with one to six carbon atoms. The alkyl groups in all of the above compounds and groups can be branched or unbranched.

All physiologically compatible acid addition salts of the compound of formula (I) with organic or inorganic acids, such as hydrochloric acid, sulfuric acid, hydrobromic acid or acetic acid, can be used in the compositions for permanent shaping of hair according to the invention.

In particularly preferred embodiments the at least one cysteine ester of the formula (I) is L-cysteine-(2-hydroxyethyl)ester and L-cysteine-(2-methoxyethyl)ester and their chloride salts.

The cysteine ester of formula (I) can however also be used with other keratin-reducing materials—such as thioglycolic acid, thiolactic acid, 3-hydroxy-2-mercaptopropionic acid, cysteamine and cysteamine derivatives or cysteine and cysteine derivatives, however the use of the cysteine esters of formula (I) as the sole keratin-reducing agent (that means without addition of other keratin-reducing agents) is particularly preferred.

The cysteine ester of formula (I) or its acid addition salts is used in the ready-to-use composition for permanent shaping of hair in an amount of from 4 to 30 percent by weight, advantageously from 8 to 28 percent by weight.

The ready-to-use composition for permanent shaping of hair according to the invention has a pH of from 4.5 to 9.0, advantageously from 6.0 to 8.5.

The hair shaping composition according to the invention can be in the form of an aqueous solution or an emulsion and also in thickened form on an aqueous basis, particularly as a gel, cream or paste.

Understandably conventional cosmetic additives can be used in the hair shaping composition according to the invention, e.g. thickeners, such as kaolin, bentonite, fatty acids, higher fatty alcohols, starch, polyacrylic acid and its derivatives, cellulose derivatives, alginate, vaseline or paraffin oil; wetting agent or emulsifier from the classes of anioinic, cationic, amphoteric or nonionic surface active compounds, particularly fatty alcohol sulfates, fatty alcohol ether sulfates, alkyl sulfonates, alkylbenzene sulfonates, quaternary ammonium salts, alkyl betaine, ethoxylated alkylphenols, fatty acid alkanol amides or ethoxylated fatty acid esters; tubidity-inducing agents, such as polyethylene glycol ester; or alcohols, especially ethanol, propanol, isopropanol or glycerin; solvating agents; stabilizers; buffer substances; perfume oils; dyes and hair conditioning and hair care components, such as cationic polymers, lanolin derivates, cholesterin, pantothenic acids or betaine. The above-mentioned cosmetic additives or ingredients are present in amounts sufficient to accomplish their purpose, for example the wetting agents and emulsifiers are present in concentrations of 0.2 to 30 percent by weight in the hair shaping composition of the invention, while the thickeners are present in an amount of 0.5 to 20 percent by weight.

A promoter substance, a so-called swelling and penetrating agent, such as dipropylene glycolmonomethyl ether, 2-pyrrolidone or imidazolidin-2-one, can be added to the hair shaping composition in an amount of from 2 to 30 percent by weight. Dithiocompounds, particularly dithiodiglycolic acid, dithiodilactic acid or their salts, can be added to the hair shaping composition according to the invention to avoid over-curling of the hair.

Since carboxylic acid esters can be kept in aqueous media only for a limited time and, especially in alkaline media, are easily hydrolyzed, the cysteine ester of formula (I) is advantageously packaged in water-free form and the hair shaping composition according to the invention is prepared by mixing the component containing the cysteine ester with one or more other components immediately prior to use.

Accordingly the agent or hair shaping composition according to the invention can be packaged in the form of a two- or three-component preparation.

Thus the hair shaping means according to the invention can be provided by mixing two components, of which the first component contains the alkalizing agent, e.g. an alkali metal carbonate, ammonium carbonate, an alkali metal hydrogen carbonate or ammonium hydrogen carbonate and the previously described cosmetic additives, while the second, water-free component contains the cysteine ester of the formula (I).

Similarly it is possible to package the hair shaping agent according to the invention in the form of a three-component preparation, in which one component contains a portion of the above-described cosmetic additives and water; a second water-free component, the cysteine ester of formula (I) and the third component, perfume oil, solvent and hair care materials in aqueous solution or in a water-free form.

In all embodiments of the hair shaping composition according to the invention the previously described cosmetic additives can be contained both in an aqueous and also in a nonaqueous component.

A hair shaping composition which is universally effective for any type of hair structure can be provided by variation of the pH of the hair shaping composition according to the invention, if necessary with additional heating. This composition according to the invention provides a springy, permanent and uniform shaping of the hair from the hair roots to the hair tips.

The permanent shaping of the hair using the hair shaping composition according to the invention is performed in the standard way. Before and/or after one brings the hair into the desired shape, it is treated with the hair shaping agent, rinsed with water, then subjected to an oxidative after-treatment, rinsed with water, if necessary put in a water wave and then dried.

First the hair is washed with a shampoo and after that rinsed with water. Subsequently the hand towel-dried hair can be divided into individual strands and wound on curlers with a diameter of 5 to 30 millimeters, advantageously 5 to 15 millimeters. Then the hair is treated with an amount of hair shaping agent according to the invention which is sufficient for hair shaping, advantageously from 60 to 120 grams.

After an acting time sufficient for the permanent shaping of the hair, which amounts to from 5 to 30 minutes depending on the application temperature, the hair properties, the pH value and the shaping effectiveness of the shaping agent (10 to 30 minutes without heating; 5 to 20 minutes with heating), the hair is rinsed with water and then subjected to an oxidative after-treatment ("fixed"). The oxidative after-treatment agent is used in an amount of 80 to 100 grams according to hair feel.

Any oxidative after-treatment agent used up to now in oxidative after-treatments can be used in the oxidative after-treatment according to the invention. Examples of a suitable oxidative after-treatment agent include potassium bromate, sodium bromate, sodium perborate, urea peroxide and hydrogen peroxide. The concentration of the oxidizing agent differs depending on the application time (usually 2 to 15 minutes) and the application temperature. Normally the oxidizing agent present in the commercially available aqueous oxidative after-treatment composition amounts to from 0.5 to 10 percent by weight. The composition used for oxidative after-treatment can understandably contain additional substances, for example wetting agents, hair care materials such as cationic active polymers, weak acids, buffer substances or peroxide stabilizing agents and can be in the form of an aqueous solution, an emulsion as well as in a thickened form in aqueous media, especially in a cream, gel or paste.

Subsequently the curlers are removed. As the case may require, the curled hair can now be subjected once again to an oxidative after-treatment. Then the hair is rinsed, if necessary put in a water wave and subsequently dried.

The hair shaping composition according to the invention for shaping the hair containing the cysteine ester of the formula (I) can be obtained in the conventional way by esterification of cysteine in the present of an acid catalyst, particularly sulfuric acid, hydrochloric acid and benzene sulfonic acid, with a suitable alcohol, advantageously with heating.

The above-mentioned cysteine ester of formula (I) is comparatively highly effective for permanent shaping of hair in acidic to mildly alkaline media, has a nearly neutral odor, is easily water soluble and has an outstanding physiological compatibility as well as a good stability in water.

Some of the compounds of formula (I) are not known in the prior art literature.

Thus the invention also includes new cysteine esters of formula (I). These new cysteine esters include L-cysteine-(2-hydroxyethyl)ester (II)

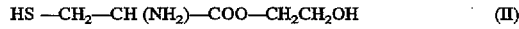

HS —CH$_2$—CH (NH$_2$)—COO—CH$_2$CH$_2$OH         (II)

and L-cysteine-(2-methoxyethyl)ester (III)

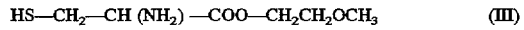

HS—CH$_2$—CH (NH$_2$) —COO—CH$_2$CH$_2$OCH$_3$         (III)

or their salts, which are particularly preferred in the hair shaping composition according to the invention, either alone or in combination with each other.

The cysteine ester of formula (I) can be made by an acid catalyzed esterification of cysteine with suitable hydroxy compounds(ethylene glycol and ethylene glycol derivatives) analogously to the following manufacturing or preperative examples.

The following examples illustrate the subject matter of the invention without limiting the invention as defined in the appended claims.

EXAMPLES

Examples of Hair Shaping Compositions

Example 1

Two Component-Hair Shaping Composition

| Component 1: | |
| --- | --- |
| 3.0 g | urea |
| 1.0 g | octylphenol, ethoxylated with 20 mole of ethylene oxide |
| 0.8 g | ammonia (25% aqueous solution) |
| 0.5 g | perfume oil |
| 0.3 g | ammonium hydrogen carbonate |
| 94.4 g | water |
| 100.0 g | |
| Component 2: | |
| 70.0 | L-cysteine-(2'-hydroxyethyl)ester |
| 30.0 g | glycerin |
| 100.0 g | |

Prior to use on the hair 70 grams of component 1 and 30 grams of component 2 are mixed to form a hair shaping composition with a pH value of 6.3.

Slightly damaged hair is washed with a shampoo and thoroughly rinsed with water. Subsequently the brushed hair is wound on a roller or curler with a diameter of 8 millimeters, moistened uniformly with this hair shaping agent and covered with a plastic bonnet. After acting for 15 minutes at 40° C. on the hair the plastic bonnet is removed, the hair is rinsed with water and oxidatively after-treated with 100 grams of a 3 percent hydrogen peroxide solution.

After removing the curlers the hair was rinsed with fresh water, put in a hair-do and then dried.

As a result of this treatment a uniform natural shaping of the hair from the hair roots to the hair tips is obtained.

Example 2

Two Component-Hair Shaping Composition

| Component 1: | |
| --- | --- |
| 2.0 g | dipropyleneglycolmonomethyl ether |
| 1.0 g | ammonia (25% aqueous solution) |
| 0.3 g | coconut fatty alcohol, ethoxylated with 10 mole ethylene oxide |
| 0.3 g | perfume oil |
| 0.2 g | diammonium dithiodiglycolate |
| 96.2 g | water, desalinated |
| 100.0 g | |
| Component 2: | |
| 60.0 | L-cysteine-(2-hydroxyethyl)ester |
| 30.0 g | glycerin |
| 10.0 g | N-acetylcysteamine |
| 100.0 g | |

80 grams of component 1 are mixed with 40 grams of component 2 to form a ready-to-use hair shaping composition having pH 6.5.

Normal undamaged hair is washed, rubbed with a hand towel and wound on curlers with a diameter of 6 millimeters. Subsequently the hair is uniformly moistened with the above-described hair shaping composition. After acting on the hair for 20 minutes the hair is thoroughly rinsed with water and then after-treated with 80 grams of a 3 percent by weight aqueous hydrogen peroxide solution. After removing the curlers the hair is rinsed with fresh water, put in a water wave and subsequently dried.

The hair so shaped has a uniform curl over the entire hair length, which is comparable with the curl obtained by treatment with mildly alkaline hair shaping compositions.

Example 3

Three Component-Hair Shaping Composition

| Component 1: | 1.9 g | 1,2-propyleneglycol |
| --- | --- | --- |
| | 1.0 g | glycerol diacetate |
| | 0.8 g | coconut fatty alcohol, ethoxylated with 10 mole ethylene oxide |
| | 0.3 g | perfume oil |
| Component 2: | 4.0 g | urea |
| | 1.5 g | ammonia (25% aqueous solution) |
| | 1.2 g | ammonium hydrogen carbonate |
| | 89.3 g | water, desalinated |
| Component 1 + 2 | 100.0 g | |
| Component 3: | 80.0 g | L-cysteine-(2-methoxyethyl)ester |
| | 20.0 g | glycerin |
| | 100.0 g | |

Component 1 is dissolved in component 2 immediately prior to useage. Then 70 grams of this solution are mixed with 30 grams of component 3. The ready-to-use permanent shaping composition ha a pH of 6.8.

Hair of unequal hair quality is washed, rubbed with a hand towel and wound on curlers with a diameter of 6 millimeters. Then the hair is uniformly moistened with the above-described -ready-to-use permanent shaping composition.

After an acting time of 15 minutes at 40° C. on the hair is rinsed with water and oxidatively after-treated with 80 grams of a 3 percent hydrogen peroxide solution. After removing the curlers the hair was rinsed with fresh water, put in a water wave and then dried.

As a result of this treatment a uniform shaping of hair with a comparatively higher springiness and elasticity is obtained.

Examples of Methods of Making L-cysteine Esters

Example 4

L-cysteine-(2-hydroxyethyl)ester.HCl

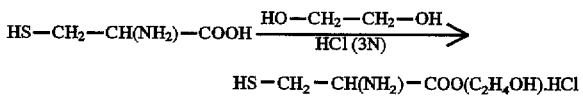

$$HS-CH_2-CH(NH_2)-COO(C_2H_4OH).HCl$$

12.1 g (0.1 mol) L-cysteine are heated in 100 ml ethylene glycol with 50 ml 3N hydrochloric acid for 18 hours under reflux. Subsequently the reaction mixture is poured into 50 ml water and then the ethylene glycol and/or its azeotrope with water is distilled off under reduced pressure. The residue is mixed with 150 ml tetrahydrofuran. The mixture obtained is then heated to boiling. After cooling a solid product is obtained by vacuum filtration, washed with tetrahydrofuran and dried in a desiccator.

The yield of this product amounted to 17.8 g(88% of the theoretical value) of a colored crystalline product, which melted at 152° to 157° C.

| CHN Analysis: $C_5H_{11}NO_3S \cdot HCl$ | | | |
|---|---|---|---|
| (MG analysis) | % C | % H | % N |
| Theoretical: | 29.78 | 6.00 | 6.95 |
| Measured: | 29.81 | 5.99 | 6.91 |

$^1$H-NMR (in $D_2O$): δ=4.33 (t;1H); 4.22(m;2H); 3.68 (m;2H); 3.08 (m;1H)

FAB-MS (matrix=glycerin): m/z=166 ($M^{+1}$); 134; 122; 93; 76.

Example 5

L-cysteine-(2-hydroxyethyl)ester.HCl

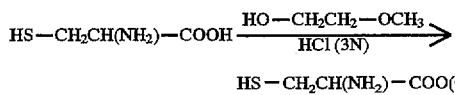

$$HS-CH_2CH(NH_2)-COO(C_2H_4OCH_3) \cdot HCl$$

12.1 g (0.1 mol) L-cysteine are heated in 100 ml methoxyethanol with 50 ml 3N hydrochloric acid for 18 hours under reflux. Subsequently the water produced by the reaction and the methoxymethanol are distilled off under reduced pressure.

The white residue is taken into 100 ml ethanol and then is precipitated in several fractions with diethyl ether.

The first fraction contains 8.0 g L-cysteine.HCl while the second fraction contains 1.0 g L-cysteine-(2-methoxyethyl)-ester.HCl which is contaminated with a slight amount of L-cysteine.HCl.

Yield: 1.0 g (4.6 % theoretical yield) L-cysteine-(2-methoxyethyl)ester

FAB-MS (Matrix=glycerin): m/z=180($M^{+1}$); 166; 122; 93; 76.

All percents herein are percents by weight.

While the invention has been illustrated and described as embodied in compositions for permanent shaping of hair and new hair keratin-reducing L-cysteine esters, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A hair shaping composition for permanent shaping of hair containing at least one reducing agent selected from the group consisting of cysteine esters of the formula (I):

$$HS-CH_2-CH(NH_2)-COO-CH_2-CH_2-R \qquad (I)$$

as a keratin-reducing material, wherein R is selected from the group consisting of a hydroxy group, alkoxy groups, poly(alkoxy) groups and hydroxypoly(alkoxy) groups; and acid additional salts of said cysteine esters of the formula (I).

2. The hair shaping composition as defined in claim 1, wherein said alkoxy groups contain from one to six carbon atoms, said poly(alkoxy) groups have the formula {O—($C_1$-$C_6$-alkyl)}$_n$H with n from 2 to 20 and said hydroxypoly (alkoxy) groups have the formula {O—($C_1$-$C_6$-alkyl)}$_m$OH with m from 1 to 20.

3. The hair shaping composition as defined in claim 1, wherein said cysteine esters are selected from the group consisting of L-cysteine-(2-hydroxyethyl)ester and L-cysteine-(2-methoxyethyl)ester; and said acid addition salts are selected from the group consisting of a hydrochloride salt of L-cysteine-(2-hydroxyethyl)ester and a hydrochloride salt of L-cysteine-(2-methoxyethyl)ester.

4. The hair shaping composition as defined in claim 1, wherein said keratin-reducing material consists of said at least one reducing agent and containing no additional keratin-reducing material.

5. The hair shaping composition as defined in claim 1, containing from 4 to 30 percent by weight of said at least one reducing agent.

6. The hair shaping composition as defined in claim 1, having a pH of from 4.5 to 9.0.

7. The hair shaping composition as defined in claim 1 comprising at least two separately packaged components, including a first component containing no water and said at least one reducing agent and at least one other component.

8. The hair shaping composition as defined in claim 7, wherein said at least one other component contains water, at least one cosmetic additive and an alkalizing agent.

9. The hair shaping composition as defined in claim 8, wherein said alkalizing agent is selected from the group consisting of ammonium carbonate, ammonium hydrogen carbonate, alkali metal hydrogen carbonates and alkali metal carbonates.

10. Cysteine esters of the formula (I):

$$HS-CH_2-CH(NH_2)-COO-CH_2-CH_2-R \qquad (I),$$

wherein R is selected from the group consisting of a hydroxy group, alkoxy groups, poly(alkoxy) groups and hydroxypoly (alkoxy) groups.

11. The cysteine esters as defined in claim 10, wherein said alkoxy groups contain from one to six carbon atoms, said poly(alkoxy) groups are of the formula {O—($C_1$-$C_6$-alkyl)}$_n$H with n from 2 to 20 and said hydroxypoly(alkoxy) groups are of the formula {O—($C_1$-$C_6$-alkyl)}$_m$OH with m from 1 to 20.

12. L-cysteine-(2-hydroxyethyl)ester.

13. L-cysteine-(2-methoxyethyl)ester.

14. Acid additional sales of said cysteine esters of the formula (I) as defined in claim 10.

15. Acid addition salts of said cysteine esters of the formula (I) as defined in claim 10 selected from the group consisting of hydrochloride salts of said cysteine esters of the formula (I), hydrobromide salts of said cysteine esters of the formula (I), sulfate salts of said cysteine esters of the formula (I) and acetate salts of said cysteine esters of the formula (I).

16. A hydrochloride salt of L-cysteine-(2-hydroxyethyl) ester.

17. A hydrochloride salt of L-cysteine-(2-methoxyethyl) ester.

* * * * *